(12) United States Patent
Miskie

(10) Patent No.: US 7,090,666 B2
(45) Date of Patent: Aug. 15, 2006

(54) MOISTURE MANAGEMENT INCONTINENCE DEVICE

(76) Inventor: Mark Miskie, 815 Stargard Ct., Charlotte, NC (US) 28270

( * ) Notice: Subject to any disclaimer, the term of this patent is extended or adjusted under 35 U.S.C. 154(b) by 0 days.

(21) Appl. No.: 10/983,477

(22) Filed: Nov. 8, 2004

(65) Prior Publication Data

US 2005/0273068 A1 Dec. 8, 2005

Related U.S. Application Data

(63) Continuation of application No. PCT/US04/17896, filed on Jun. 4, 2004.

(51) Int. Cl.
*A61F 13/15* (2006.01)
(52) U.S. Cl. .............. 604/385.14; 604/385.11; 604/385.19; 604/393; 604/395; 604/402
(58) Field of Classification Search ............ 604/379, 604/380, 385.01, 385.101, 385.14, 385.15, 604/385.19, 385.03, 385.11, 385.13, 393, 604/395, 399, 402
See application file for complete search history.

(56) References Cited

U.S. PATENT DOCUMENTS

| | | | | |
|---|---|---|---|---|
| 4,961,736 A | * | 10/1990 | McCloud | 604/385.15 |
| 5,069,672 A | | 12/1991 | Wippler et al. | |
| 5,360,422 A | * | 11/1994 | Brownlee et al. | 604/385.15 |
| 5,613,959 A | * | 3/1997 | Roessler et al. | 604/364 |
| 5,707,364 A | * | 1/1998 | Coates | 604/391 |
| 6,423,047 B1 | * | 7/2002 | Webster | 604/385.15 |
| 6,989,005 B1 | * | 1/2006 | LaVon et al. | 604/385.14 |

* cited by examiner

*Primary Examiner*—Jacqueline F. Stephens
(74) *Attorney, Agent, or Firm*—Schwartz Law Firm P.C.

(57) ABSTRACT

A moisture management incontinence pad is adapted for placement within an undergarment worn by a user. The fabric composite includes a plurality of overlying absorbent layers having respective first and second opposing end edges and first and second opposing side edges. The adsorbent layers are substantially unattached to one another along at least one of respective first and second side edges and first and second end edges to promote circulation between the layers during laundering. A liquid impermeable jacket resides adjacent an outside major surface of the fabric composite, and covers the opposing end edges and opposing side edges of the absorbent layers. The jacket is adapted for trapping moisture within the composite, and forms a moisture barrier between the composite and the undergarment. The jacket defines an open moisture entry zone which communicates with a portion of the inside major surface of the fabric composite, whereby moisture is received through the entry zone and into the fabric composite for transport away from the body of the user.

19 Claims, 7 Drawing Sheets

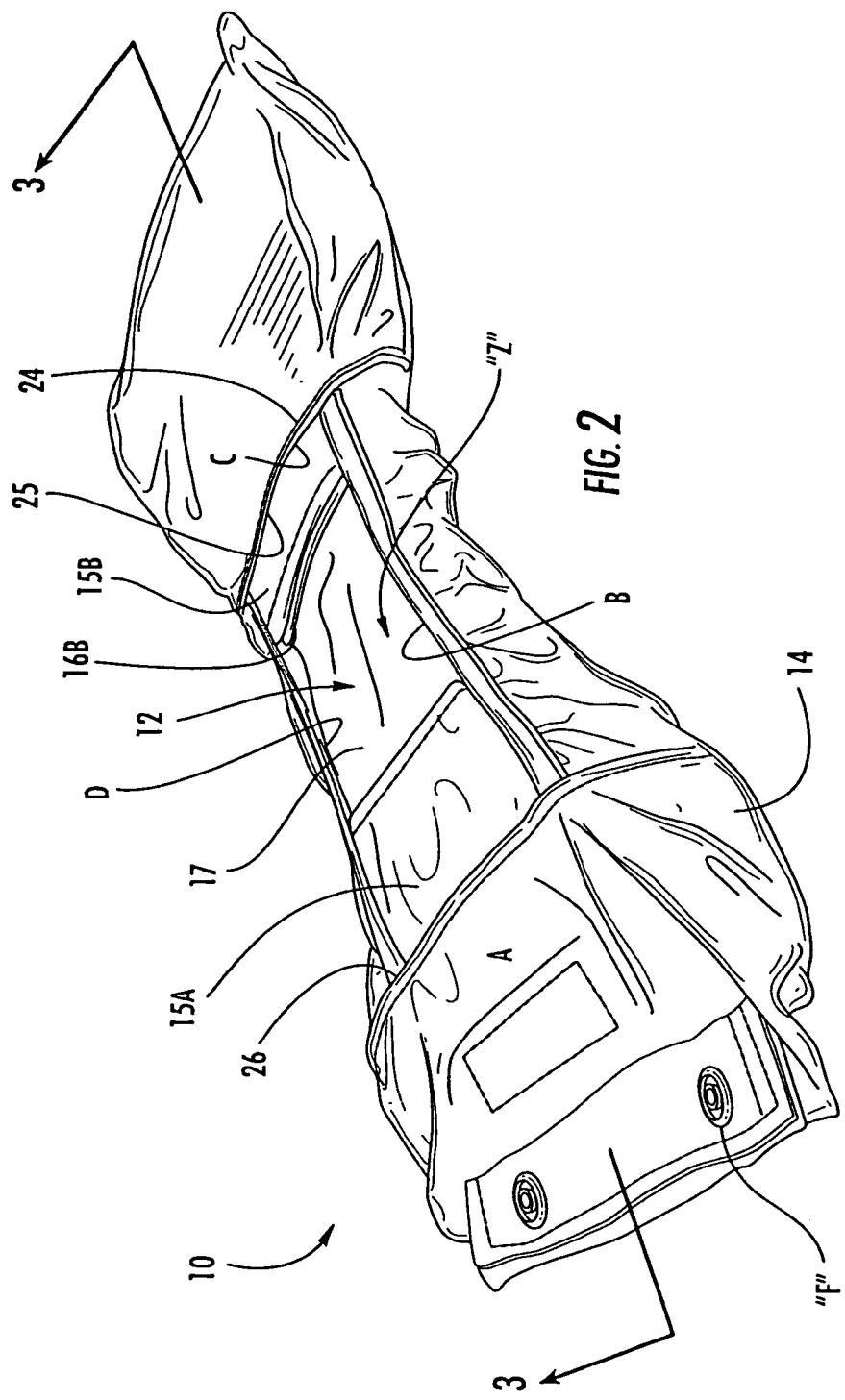

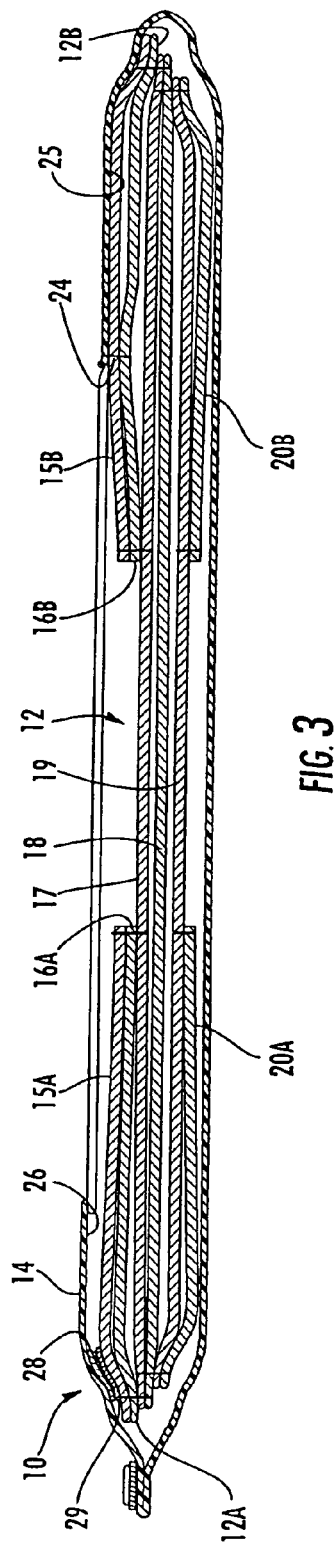
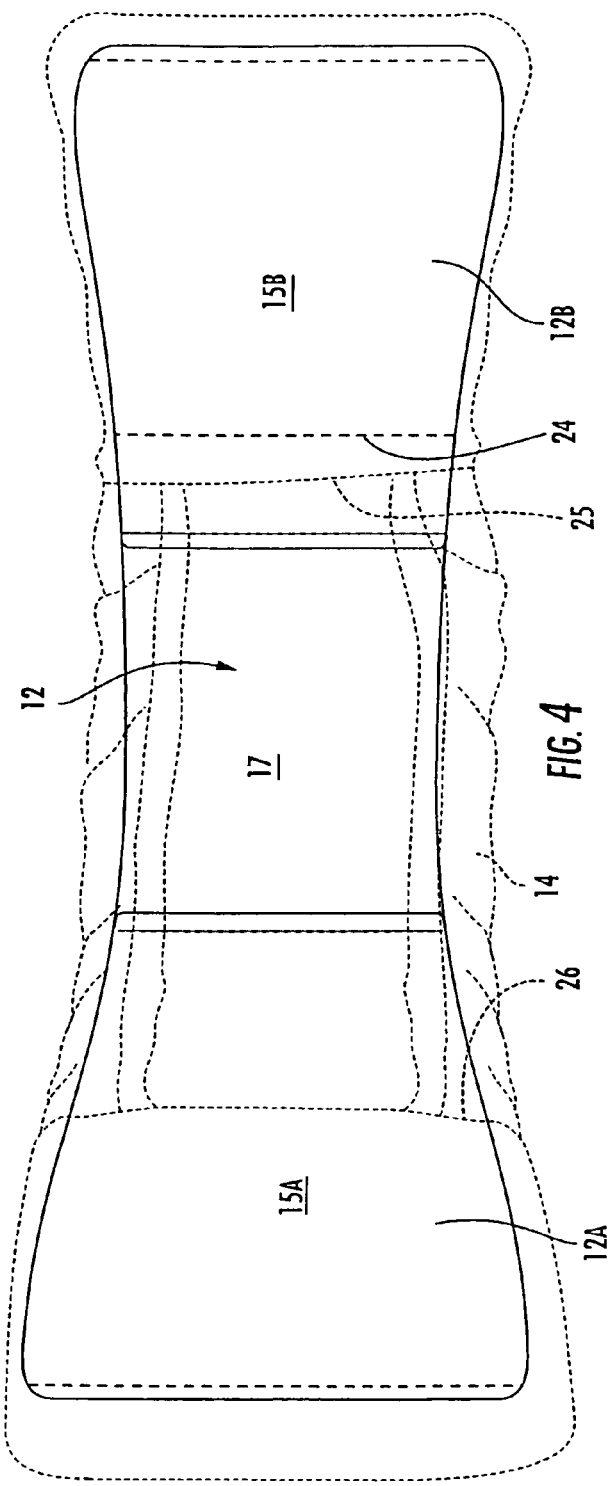

MOISTURE MANAGEMENT INCONTINENCE DEVICE

TECHNICAL FIELD AND BACKGROUND OF THE INVENTION

This invention relates to a moisture management incontinence pad designed for both men and women, and applicable for managing light, moderate and heavy urinary incontinence. The invention is especially useful for controlling multiple instances of leakage.

An estimated 19 million North American adults suffer urinary incontinence with severity ranging from partial to complete loss of bladder control. They may experience varying degrees of urine loss, and the incontinence may change over time. For example, some adults with light incontinence may leak a little when they laugh or cough, while others with heavy incontinence may be experience continuous leakage. No two cases are alike, and no two adults are affected by incontinence the same way.

Incontinence is not an inevitable part of aging, and it is not a disease. In fact, in most cases, it is merely a symptom or side-effect of another medical condition. Male urinary incontinence may be caused by any number of health conditions including prostate surgery, neurologic disease or injury (Parkinson's disease, stroke or spinal cord injury), obstructed urination, and certain birth defects or chronic medical conditions such as diabetes. In many cases, incontinence can be cured and it can always be managed. Many women will experience periods of urinary incontinence caused by childbirth and menopause.

Presently available commercial products address all levels of urinary incontinence. Prior art incontinence pads are generally either relatively inexpensive and disposable, or more expensive and reusable. The present invention focuses on the reusable pad market. Such pads typically include a moisture absorbing component combined with an overlying moisture barrier. The moisture barrier is designed to prevent movement of moisture through the moisture absorbing component and outwardly from the pad. When washing these pads for reuse, it is difficult to fully clean the moisture absorbing component due to the restricted flow of water through the pad caused by the moisture barrier. An even greater problem is the inability to efficiently and effectively dry the pad after washing. Thus, while an advantage of these pads lies in their repeated reusability, the considerable time and inconvenience in laundering generally outweighs the ultimate costs savings.

SUMMARY OF INVENTION

Therefore, it is an object of the invention to provide a moisture management incontinence pad which is launderable and reusable.

It is another object of the invention to provide a moisture management incontinence pad which can be efficiently and effectively cleaned.

It is another object of the invention to provide a moisture management incontinence pad which can be efficiently and effectively dried after washing.

It is another object of the invention to provide a moisture management incontinence pad which can be either used alone or in combination with a washable undergarment.

It is another object of the invention to provide a moisture management incontinence pad which promotes rapid osmotic pulling or wicking of moisture away from the skin of a user.

It is another object of the invention to provide a moisture management incontinence pad which utilizes a first wicking layer at a urine entry zone and then multiple layers of increasingly absorbent fabric.

It is another object of the invention to provide a moisture management incontinence pad which can be worn over an extended period of time.

It is another object of the invention to provide a moisture management incontinence pad which is specifically intended to receive and properly manage multiple instances of urine leakage without having to change the pad.

It is another object of the invention to provide a moisture management incontinence pad which is constructed such that all fabric layers including the outer barrier jacket are adjoined to ensure proper orientation when reconstructing the pad after laundering.

These and other objects of the present invention are achieved in the preferred embodiments disclosed below by providing a moisture management incontinence pad adapted for placement within an undergarment worn by a user. The incontinence pad includes a multi-layer fabric composite having an inside major surface for residing nearest the body of the user and an outside major surface for residing nearest the undergarment. The fabric composite comprises a plurality of overlying absorbent layers having respective first and second opposing end edges and first and second opposing side edges. The adsorbent layers are substantially unattached to one another along at least one of respective first and second side edges and first and second end edges to promote circulation between the layers during laundering. The term "substantially unattached" as used herein means unattached along more than 50% of the entire length of a single side edge or end edge, and preferably more than 80% of the entire length of the side edge or end edge. The term "laundering" is broadly defined herein to mean any step in the cleaning process including washing and air drying.

A liquid impermeable jacket resides adjacent the outside major surface of the fabric composite, and covers the opposing end edges and opposing side edges of the absorbent layers. The jacket is adapted for trapping moisture within the composite, and forms a moisture barrier between the composite and the undergarment. The jacket defines an open moisture entry zone which communicates with a portion of the inside major surface of the fabric composite, whereby moisture is received through the entry zone and into the fabric composite for transport away from the body of the user.

According to another preferred embodiment of the invention, the liquid impermeable jacket covers greater than 20 percent of the inside major surface of the fabric composite.

According to another preferred embodiment of the invention, the moisture entry zone occupies less than 80 percent of the inside major surface.

According to another preferred embodiment of the invention, the absorbent layers are attached together at respective first and second end edges.

According to another preferred embodiment of the invention, the absorbent layers are substantially unattached to one another along respective first and second side edges.

According to another preferred embodiment of the invention, the fabric composite has a fixed end secured to the jacket and a free end opposite the fixed end.

According to another preferred embodiment of the invention, the jacket has a lateral pocket for receiving the free end of the fabric composite.

According to another preferred embodiment of the invention, means are provided for releasably attaching the free end of the fabric composite inside the pocket of the jacket, such that the fabric composite is removable from the pocket and extendable outwardly from the jacket for laundering and drying.

According to another preferred embodiment of the invention, the means for releasably attaching the free end of the fabric composite includes mating hook and loop fasteners.

According to another preferred embodiment of the invention, the inside major surface of the fabric composite includes hydrophobic fibers.

According to another preferred embodiment of the invention, the fabric composite includes at least 4 overlying absorbent layers.

According to another preferred embodiment of the invention, the fabric composite has an hourglass design.

According to another preferred embodiment of the invention, the fabric composite has a reduced thickness at a tapered portion of the hourglass design.

According to another preferred embodiment of the invention, the jacket has opposing elastic side edges.

In another embodiment, the invention is an undergarment combined with a moisture management incontinence pad, as described above, placed inside the undergarment and adjacent the body of a user.

In yet another embodiment, the invention is a method for managing moisture resulting from moderate to heavy incontinence.

BRIEF DESCRIPTION OF THE DRAWINGS

Some of the objects of the invention have been set forth above. Other objects and advantages of the invention will appear as the description proceeds when taken in conjunction with the following drawings, in which:

FIG. 2 is a perspective view of the incontinence pad;

FIG. 3 is a cross-sectional view of the incontinence pad taken substantially along line 3—3 of FIG. 2;

FIG. 4 is a top view of the fabric composite with the outer jacket shown in phantom;

DESCRIPTION OF THE PREFERRED EMBODIMENT AND BEST MODE

Figure 1:
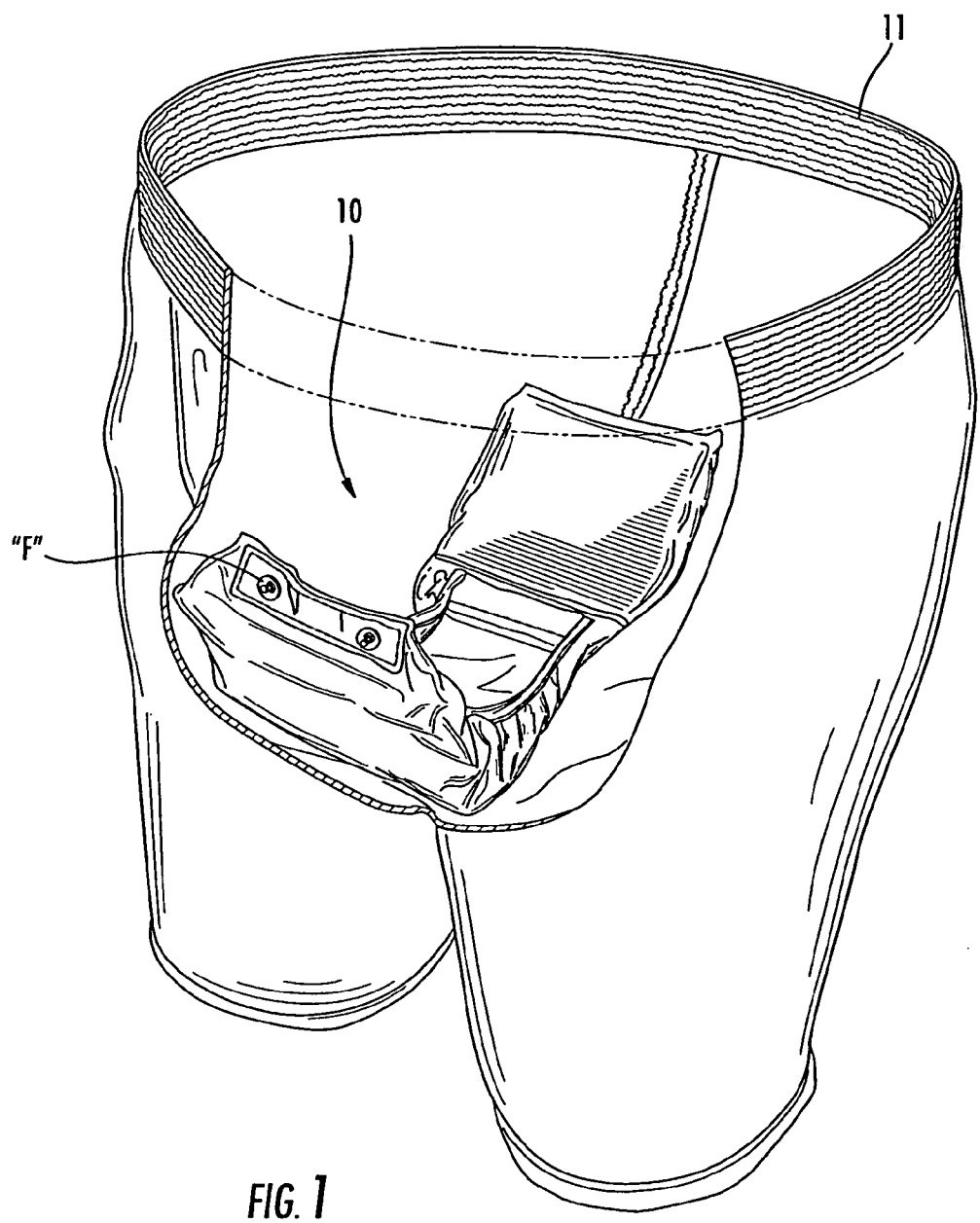
FIG. 1 is an environmental perspective view of the moisture management incontinence pad according to one preferred embodiment of the present invention.

Referring now specifically to the drawings, a moisture management incontinence pad according to the present invention is illustrated in FIG. 1, and shown generally at reference numeral 10. The incontinence pad 10 is designed for both men and women, and is especially useful for wear at night to manage multiple instances of moderate to heavy urine leakage while sleeping. The incontinence pad 10 is adapted for suspension inside an undergarment 11 using any suitable fastener "F", such as snaps, hook and loop fasteners, or the like. The undergarment 11 resembles a conventional sport brief including an elastic waistline, a front and rear joined to the waistline, and first and second leg segments defining respective leg openings. The undergarment 11 has complementary fasteners (not shown) designed to mate with the fasteners "F" of the incontinence pad 10 to position and retain the pad 10 inside the undergarment 11.

As best shown in FIGS. 2 and 3, the incontinence pad 10 comprises a multi-layer fabric composite 12 substantially encased within a liquid impermeable, vapor permeable polyester jacket 14. The fabric composite 12 has an inside major surface which resides nearest the body of the user, and an outside major surface which resides nearest the undergarment 11. A first layer 15A, 15B of the fabric composite 12 includes soft hydrophilic or wicking fibers, such as Dacron® manufactured by E. I. du Pont de Nemours and Company. The wicking fibers operate to quickly move moisture away from the skin and into an overlying series of more absorbent inner layers 16A, 16B, 17, 18, 19, 20A, 20B. The inner layers 16A, 16B, 17, 18, 19, 20A, 20B comprise hydrophilic fibers, such as cotton, hydrophilic nylon, rayon, wool, and blends of these fibers.

The liquid impermeable, vapor permeable jacket 14 resides adjacent the outside major surface of the fabric composite 12, and covers the end edges and opposing side edges of the composite layers 15A, 15B, 16A, 16B, 17, 18, 19, 20A, 20B. The sides of the jacket 14 comprise elastic yarns, such as Spandex®, which give the incontinence pad 10 a generally cupped shape for improved fit and added comfort. The jacket 14 serves to trap liquid within the fabric composite 12, and forms a breathable moisture barrier between the composite 12 and the undergarment 11.

Urine enters the incontinence pad 10 through a moisture entry zone "Z" which communicates with an entirely exposed portion of the inside major surface of the fabric composite 12. As shown in FIG. 2, the moisture entry zone "Z" is defined by an area of the fabric composite 12 extending between points A, B, C, and D of the jacket 14. Preferably, the jacket 14 wraps around the ends and sides of the fabric composite 12 covering greater than 20 percent of the inside major surface, thereby reducing the likelihood of urine leakage outwardly from the incontinence pad 10 and onto the undergarment 11 and bed sheets. In this embodiment, the moisture entry zone "Z" comprises less than 80 percent of the inside major surface of the fabric composite. During each incidence of leakage, urine is received through the entry zone "Z" and immediately passed into the fabric composite 12 for transport away from the body.

Referring to FIGS. 3 and 4, the fabric composite 12 comprises an assembly of full length and partial length fabric layers 17, 18, 19 and 15A, 15B, 16A, 16B, 20A, 20B, respectively. The full length fabric layers 17, 18, 19 extend in overlying registration from one end of the fabric composite 12 to the other and have a generally hourglass design. Each of the layers 17, 18, 19 has opposing relatively wide ends tapering at a narrow center. The partial length layers 15A, 15B, 16A, 16B and 20A, 20B overlie respective wide ends of the layers 17 and 19, such that the fabric composite 12 is relatively thick and wide at the ends and relatively thin and narrow at the center. Preferably, the front end 12A of the fabric composite 12 is wider than the rear end 12B, and may include additional partial fabric layers (not shown) for increased moisture absorption.

The partial length layers 15A, 15B, 16A, 16B and 20A, 20B are sewn together at respective opposite ends to the full length layers 17 and 19, as best shown in FIG. 3. Additionally, the layers 15B and 16B are sewn together to the jacket 14 at an intermediate point 24. The full length layers 17, 18, 19 are sewn to the partial length layers 15A, 15B, 16A, 16B, 20A, 20B at respective opposite ends of the layers 17, 18, 19. The opposing sides of all layers 15A, 15B, 16A, 16B, 17, 18, 19, 20A, 20B remain substantially unattached in order to promote air circulation through the fabric composite 12 between adjacent layers. Preferably, the individual layer ends at respective opposite ends 12A and 12B of the fabric composite 12 are staggered in pairs, thereby thinning the composite 12 at the ends 12A, 12B for added comfort.

Figure 5:
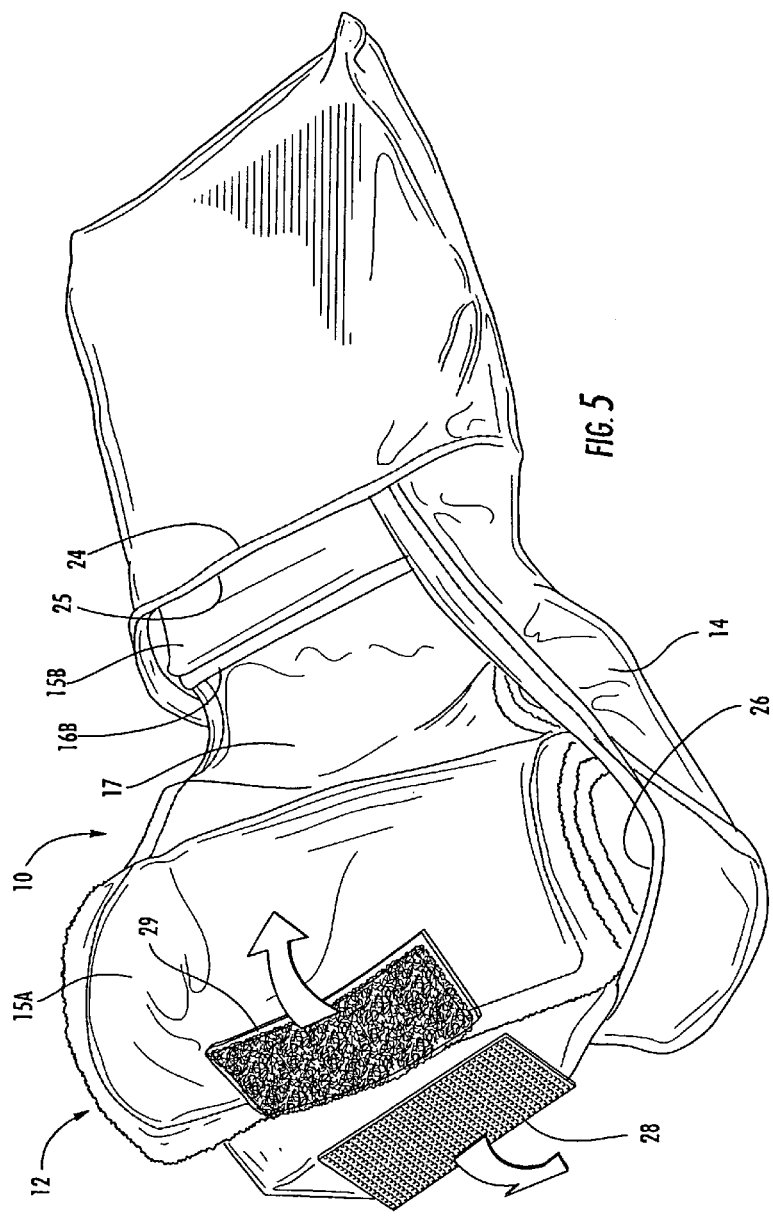
FIG. 5 is a perspective view the incontinence pad showing the fabric composite being detached and removed from the jacket pocket.
Figure 6:
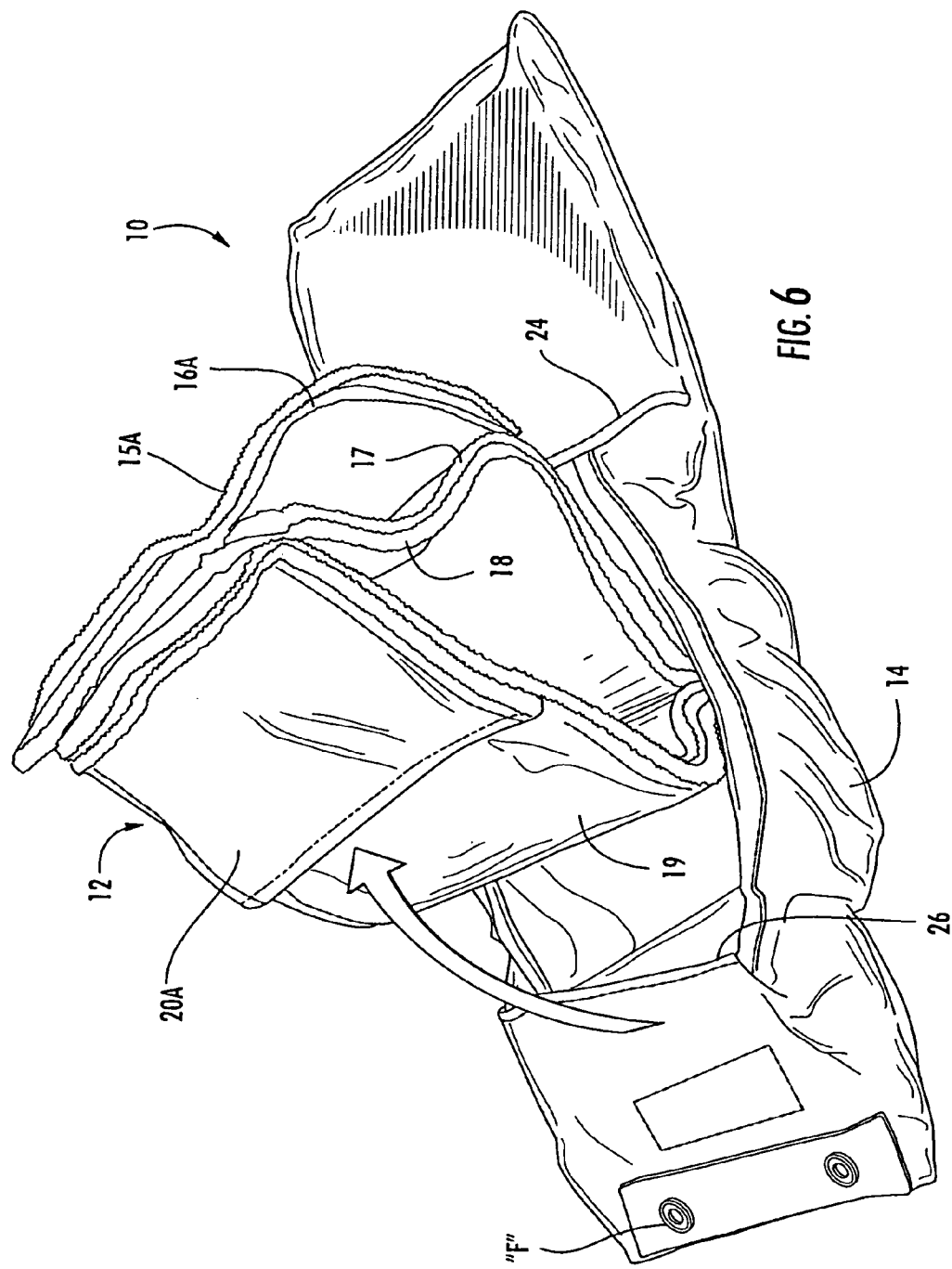
FIG. 6 is a perspective view of the incontinence pad showing the fabric composite pulled away from the jacket pocket in preparation for laundering.

The fixed end 12B of the fabric composite 12 resides within a lateral end pocket 25 of the jacket 14 and is permanently secured to the jacket 14 at point 24, as previously described. The free end 12A of the fabric composite 12 is received inside a second lateral end pocket 26 of the jacket 14. As shown in FIG. 5, the free end 12A is releasably secured to the jacket 14 by complementary patches of hook and loop fasteners 28 and 29. Prior to washing and drying the incontinence pad 10, the free end 12A of the fabric composite 12 is removed from the end pocket 26 and extended away from the jacket 14, as illustrated in FIG. 6. The attached fabric layers 15A, 15B, 16A, 16B, 17, 18, 19, 20A, 20B open along respective opposite sides to allow effective cleaning of the interior layers, and to promote fast and efficient drying. After laundering, the fabric composite 12 is replaced inside the end pocket 26 of the jacket 14 and the complementary hook and loop fasteners 28, 29 reattached.

For increased absorption, one or more separate, unattached layers of fabric may be added inside the jacket 14 at any desired location. In an alternative embodiment, the entire fabric composite 12 may be removable from the jacket 14 and constructed for ready and convenient re-insertion into the jacket.

Figure 7:
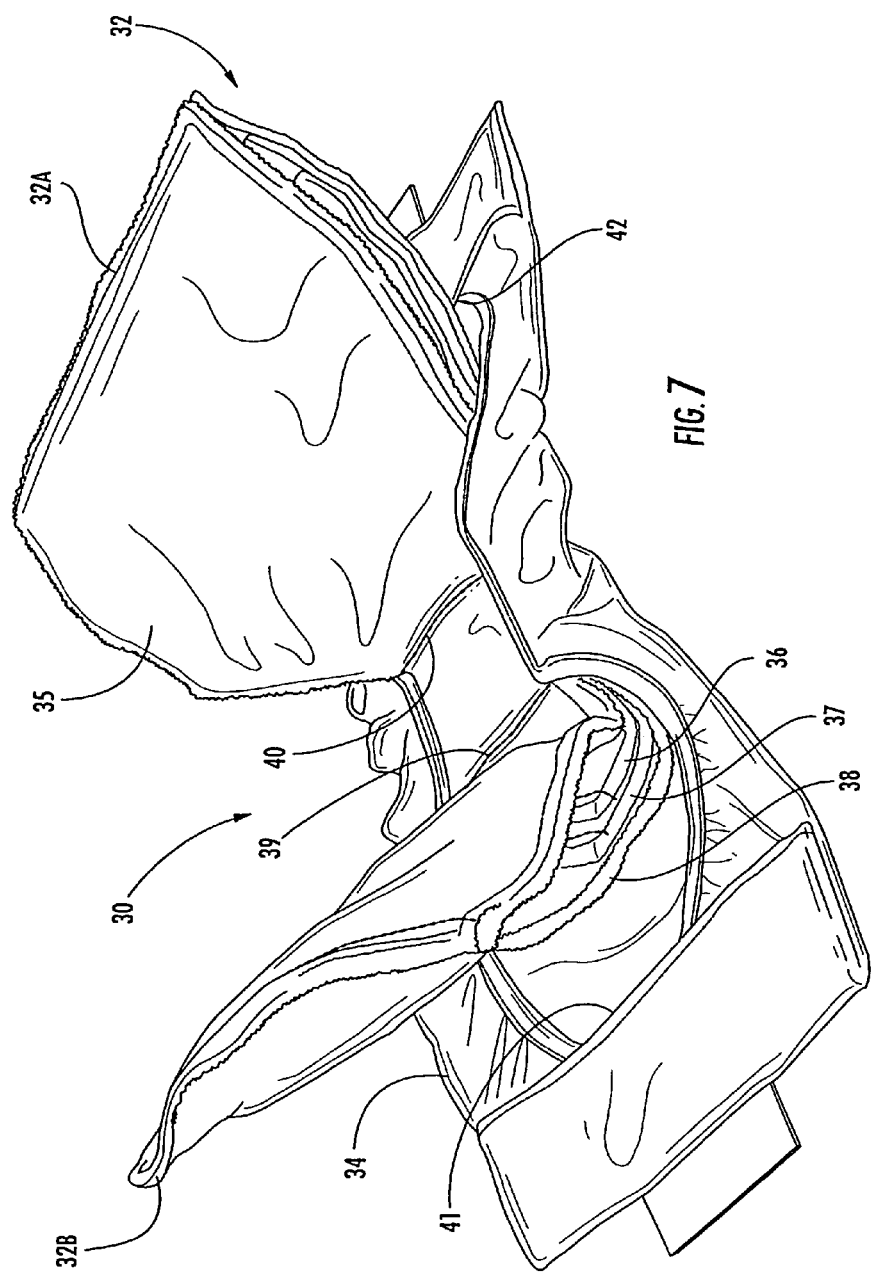
FIG. 7 is a perspective view of the incontinence pad according to a second preferred embodiment, and showing opposite ends of the fabric composite pulled away from the jacket pockets.
Figure 8:
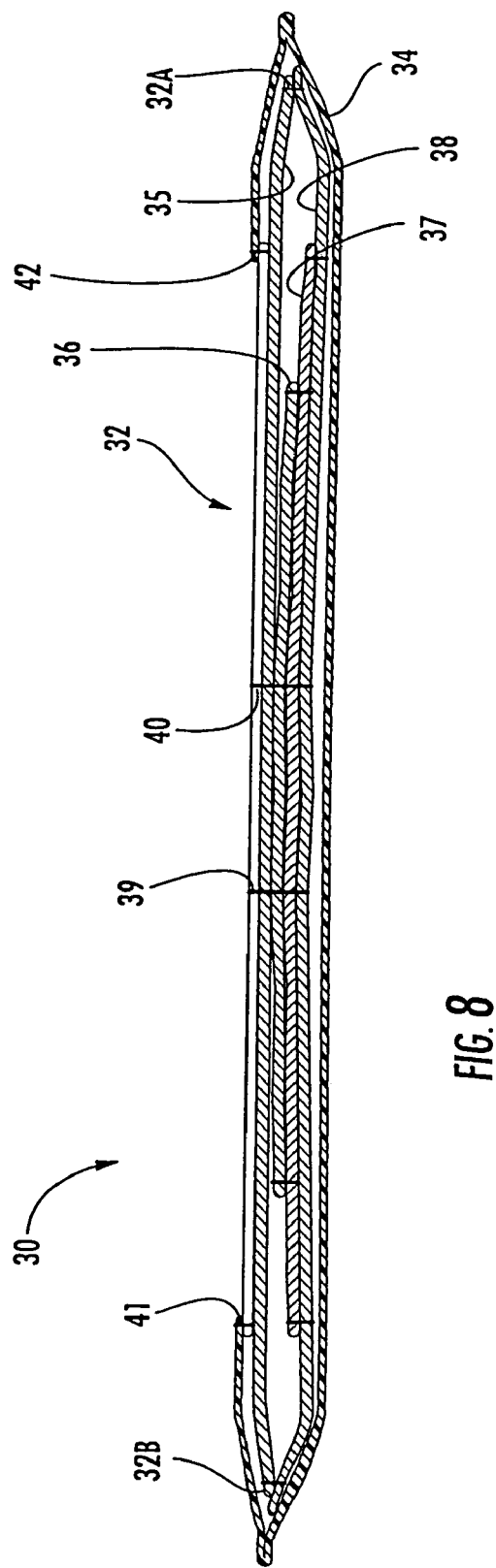
FIG. 8 is a cross-sectional view of the incontinence pad shown in FIG. 7.

A further embodiment of an incontinence pad 30 according to the present invention is illustrated in FIGS. 7 and 8. The incontinence pad 30 comprises a multi-layer fabric composite 32 substantially encased within a liquid impermeable, vapor permeable polyester jacket 34. The fabric composite 32 has an inside major surface which resides nearest the body of the user, and an outside major surface which resides nearest the undergarment (not shown). A first layer 35 of the fabric composite 32 includes soft hydrophilic or wicking fibers, such as Dacron® manufactured by E. I. du Pont de Nemours and Company. The wicking fibers operate to quickly move moisture away from the skin and into an overlying series of more absorbent inner layers 36, 37, and 38. The inner layers 36, 37, 38 comprise hydrophilic fibers, such as cotton, hydrophilic nylon, rayon, wool, and blends of these fibers.

The liquid impermeable, vapor permeable jacket 34 resides adjacent the outside major surface of the fabric composite 32, and covers the end edges and opposing side edges of the composite layers 35, 36, 37, and 38. The side edges of the jacket 34 comprise elastic yarns, such as Spandex®, which give the incontinence pad 30 a generally cupped shape for improved fit and added comfort. The jacket 34 serves to trap liquid within the fabric composite 32, and forms a breathable moisture barrier between the composite 32 and the undergarment.

Urine enters the incontinence pad 30 through a moisture entry zone, as previously described. Preferably, the jacket 34 wraps around the ends and sides of the fabric composite 32 covering greater than 20 percent of the inside major surface, thereby reducing the likelihood of urine leakage outwardly from the incontinence pad 30 and onto the undergarment and bed sheets. As in pad 10, the moisture entry zone comprises less than 80 percent of the inside major surface of the fabric composite 32. During each incidence of leakage, urine is received through the entry zone and immediately passed into the fabric composite 32 for transport away from the body.

As best shown in FIG. 8, the fabric composite 32 comprises an assembly of full length and partial length fabric layers—35, 36, 37, and 38. The full length fabric layers 35 and 38 extend from one end of the fabric composite 32 to the other, and are sewn together at respective opposite ends. The partial length layer 36 overlies inner layer 37 which overlies the layer 38. The layers 36, 37, and 38 are arranged in increasing lengths such that the ends of the fabric composite 32 have a relatively thin profile, while the central area at the moisture entry zone defines a thicker profile for increased absorption. Each of the layers 35–38 has opposing relatively wide ends tapering at a narrow center to form a generally hourglass design. Preferably, the front end 32A of the fabric composite 32 is wider than the rear end 32B, and may include additional partial fabric layers (not shown).

As previously stated, the full length layers 35 and 38 are sewn together at their respective opposite ends. The partial length layer 36 is sewn at its opposite ends to the underlying inner layer 37. This layer 37 is sewn at its opposite ends to the underlying layer 38. The opposing sides of all layers 35–38 remain substantially unattached in order to promote air circulation through the fabric composite 32 between adjacent layers.

Each of the layers 35–38 are sewn together and attached to the jacket 34 at the central area of the pad 30 along lateral stitch lines 39 and 40. The ends 32A and 32B of the fabric composite 32 are preferably unattached to the jacket 34, and are designed removably placement within respective lateral pockets 41 and 42. Prior to washing and drying the incontinence pad 30, the free ends 32A and 32B of the fabric composite 32 are removed from respective end pockets 41, 42 and are extended away from the jacket 34, as illustrated in FIG. 7. The attached fabric layers 35–38 open along respective opposite sides to allow effective cleaning of the interior layers, and to promote fast and efficient drying. After laundering, the fabric composite 32 is replaced inside the end pockets 41, 42 of the jacket 34 and the pad reassembled for reuse.

A moisture management incontinence pad is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. A launderable and reusable moisture management incontinence pad adapted for placement within an undergarment worn by a user, said incontinence pad comprising:

(a) a multi-layer fabric composite having an inside major surface for residing nearest the body of the user and an outside major surface for residing nearest the undergarment, said fabric composite comprising a plurality of overlying absorbent layers having respective first and second opposing end edges and first and second opposing longitudinal side edges;

(b) said absorbent layers of said fabric composite being substantially unattached to one another along respective first and second longitudinal side edges to promote circulation between said layers during laundering;

(c) a liquid impermeable jacket affixed to at least one of the absorbent layers and residing adjacent the outside major surface of said fabric composite and covering the opposing end edges and opposing side edges of said absorbent layers, said jacket adapted for trapping moisture within said composite, and forming a moisture barrier between said composite and the undergarment, and wherein said fabric composite is substantially unattached to said jacket along respective first and second longitudinal side edges of said absorbent layers and along at least one of said end edges of said fabric composite, such that prior to laundering, said fabric composite is extendable outwardly from said jacket for improved cleaning and drying of said absorbent layers; and (d) said jacket defining an open moisture entry zone communicating with a portion of the inside major surface of said fabric composite, whereby moisture is received through said entry zone and into said fabric composite for transport away from the body of the user.

2. A moisture management incontinence pad according to claim 1, wherein said liquid impermeable jacket wraps around said fabric composite and covers greater than 20 percent of its inside major surface.

3. A moisture management incontinence pad according to claim 1, wherein said moisture entry zone comprises less than 80 percent of the inside major surface of said fabric composite.

4. A moisture management incontinence pad according to claim 1, wherein said absorbent layers are attached together at respective first and second end edges.

5. A moisture management incontinence pad according to claim 1, wherein said jacket comprises opposing elastic side edges.

6. A moisture management incontinence pad according to claim 1, wherein said fabric composite comprises a fixed end secured to said jacket and a free end opposite said fixed end.

7. A moisture management incontinence pad according to claim 6, wherein said jacket comprises a lateral pocket for receiving the free end of said fabric composite.

8. A moisture management incontinence pad according to claim 7, and comprising means for releasably attaching the free end of said fabric composite inside the pocket of said jacket, such that said fabric composite is removable from the pocket and extend able outwardly from said jacket for laundering.

9. A moisture management incontinence pad according to claim 8, wherein said means for releasably attaching the free end of said fabric composite comprises mating hook and loop fasteners.

10. A moisture management incontinence pad according to claim 1, wherein the inside major surface of said fabric composite comprises hydrophobic fibers.

11. A moisture management incontinence pad according to claim 1, wherein said fabric composite comprises at least 3 overlying absorbent layers.

12. A moisture management incontinence pad according to claim 1, wherein said fabric composite comprises an hourglass design.

13. A moisture management incontinence pad according to claim 12, wherein said fabric composite comprises a reduced thickness at a tapered portion of said hourglass design.

14. A moisture management incontinence pad according to claim 1, wherein said fabric composite comprises opposing free ends unattached to said jacket.

15. A moisture management incontinence pad according to claim 14, wherein said jacket comprises lateral end pockets adapted for removably receiving respective free ends of said fabric composite, such that said fabric composite is removable from said end pockets and extend able away from said jacket for laundering.

16. A launderable and reusable moisture management incontinence pad adapted for placement within an undergarment worn by a user, said incontinence pad comprising:

(a) a multi-layer fabric composite having an inside major surface for residing nearest the body of the user and an outside major surface for residing nearest the undergarment, said fabric composite comprising a plurality of overlying absorbent layers having respective first and second opposing end edges and first and second opposing longitudinal side edges, and said absorbent layers comprising fibers selected from the group consisting of cotton, hydrophilic nylon, rayon, and wool;

(b) said absorbent layers being substantially unattached to one another along a portion of respective first and second longitudinal side edges to promote circulation between said layers during laundering;

(c) a liquid impermeable jacket affixed to at least one of the absorbent layers and residing adjacent the outside major surface of said fabric composite and covering the opposing end edges and opposing side edges of said absorbent layers, said jacket adapted for trapping moisture within said composite, and forming a moisture barrier between said composite and the undergarment, and wherein said fabric composite is substantially unattached to said jacket along respective first and second longitudinal side edges of said absorbent layers and along at least one of said end edges of said fabric composite, such that prior to laundering, said fabric composite is extendable outwardly from said jacket for improved cleaning and drying of said absorbent layers; and (d) said jacket defining an open moisture entry zone communicating with a portion of the inside major surface of said fabric composite, whereby moisture is received through said entry zone and into said fabric composite for transport away from the body of the user.

17. A moisture management incontinence pad according to claim 16, wherein said fabric composite comprises opposing free ends unattached to said jacket.

18. A moisture management incontinence pad according to claim 17, wherein said jacket comprises lateral end pockets adapted for removably receiving respective free ends of said fabric composite, such that said fabric composite is removable from said end pockets and extendable away from said jacket for laundering.

19. A moisture management incontinence pad according to claim 16, wherein said fabric composite comprises an hourglass design.

* * * * *